US011045076B2

(12) United States Patent
Kim et al.

(10) Patent No.: US 11,045,076 B2
(45) Date of Patent: Jun. 29, 2021

(54) OPTICAL PROBE WITH ROTATION MIRROR

(71) Applicant: Electronics and Telecommunications Research Institute, Daejeon (KR)

(72) Inventors: Jong Deog Kim, Daejeon (KR); Hyun Woo Song, Daejeon (KR)

(73) Assignee: Electronics and Telecommunications Research Institute, Daejeon (KR)

(*) Notice: Subject to any disclaimer, the term of this patent is extended or adjusted under 35 U.S.C. 154(b) by 111 days.

(21) Appl. No.: 16/232,636

(22) Filed: Dec. 26, 2018

(65) Prior Publication Data

US 2020/0121172 A1    Apr. 23, 2020

(30) Foreign Application Priority Data

Oct. 17, 2018   (KR) .................. 10-2018-0124018

(51) Int. Cl.
*A61B 1/01*   (2006.01)
*A61B 1/07*   (2006.01)
*A61B 1/00*   (2006.01)

(52) U.S. Cl.
CPC ...... *A61B 1/00183* (2013.01); *A61B 1/00006* (2013.01); *A61B 1/00096* (2013.01); *A61B 1/00114* (2013.01); *A61B 1/07* (2013.01); *A61B 1/00167* (2013.01)

(58) Field of Classification Search
CPC ... A61B 1/00183; A61B 1/07; A61B 1/00006; A61B 1/00114; A61B 1/00096; A61B 1/00167; A61B 5/0073; A61B 5/0084; A61B 5/1079; A61B 1/00027; A61B 1/00172; A61B 1/00177

See application file for complete search history.

(56) References Cited

U.S. PATENT DOCUMENTS

| 6,396,050 | B1* | 5/2002 | Yamamoto ............. B82Y 20/00 |
| | | | 250/216 |
| 7,991,455 | B2 | 8/2011 | Crowley et al. |
| 9,574,870 | B2 | 2/2017 | Yamazaki et al. |
| 9,638,862 | B2 | 5/2017 | Bhagavatula et al. |
| 9,877,784 | B2 | 1/2018 | Jung et al. |
| 10,905,397 | B2* | 2/2021 | Yang .................... A61B 5/0095 |
| 2008/0243002 | A1* | 10/2008 | Munce ................ A61B 5/0095 |
| | | | 600/459 |
| 2015/0272428 | A1 | 10/2015 | Nam et al. |

FOREIGN PATENT DOCUMENTS

| JP | 2011-072401 A | 4/2011 |
| KR | 10-2014-0126554 A | 10/2014 |
| KR | 10-2018-0077966 A | 7/2018 |

OTHER PUBLICATIONS

Michalina J. Gora et al., "Endoscopic optical coherence tomography: technologies and clinical applications [Invited]", Biomedical Optics Express, vol. 8, No. 5, May 1, 2017.

\* cited by examiner

*Primary Examiner* — Seung C Sohn
(74) *Attorney, Agent, or Firm* — Rabin & Berdo, P.C.

(57) ABSTRACT

Provided is an optical probe. The optical probe includes an optical input/output unit, a rotation part spaced apart from the optical input/output unit in a first direction and including a reflection surface, and a transparent electrode provided around the reflection surface.

19 Claims, 9 Drawing Sheets

OPTICAL PROBE WITH ROTATION MIRROR

CROSS-REFERENCE TO RELATED APPLICATIONS

This U.S. non-provisional patent application claims priority under 35 U.S.C. § 119 of Korean Patent Application No. 10-2018-0124018, filed on Oct. 17, 2018, the entire contents of which are hereby incorporated by reference.

BACKGROUND

The present disclosure herein relates to an optical probe and an optical probe system including the same, and more particularly, to an optical probe without a shadow section and an optical probe system including the same.

Optical probe technologies have been developed to apply Optical Coherence Tomography (OCT), Photoacoustic Tomography (PAT), Raman Spectroscopy, Fluorescence Spectroscopy, and Photodynamic Therapy (PDT) techniques to endoscopic medical devices in addition to Camera-based endoscopic medical imaging devices. For example, by laterally combining the depth scans of the axial direction in which the light travels, optical-based tomography techniques may be used as a guide for 3D endoscopic imaging or interventional procedures for internal organs of the human body. Furthermore, optical probes for spotting and scanning may be used in a spontaneous spectroscopic diagnosis of tissues near the epidermis, a precise spectroscopy diagnosis of diseased tissue combined with injected photosensitizer, or treatment techniques by irradiation of specific wavelength light.

SUMMARY

The present disclosure is to provide an optical probe capable of eliminating shading in a light irradiation section and an optical probe system including the same.

The present disclosure is to provide an optical probe capable of precisely detecting all sections without a shading section and an optical probe system including the same.

The present disclosure is to provide an optical probe capable of improving electrical characteristics such as resistance while using a transparent electrode and an optical probe system including the same.

The present disclosure is to provide an optical probe capable of obtaining an accurate image due to high speed rotation and an optical probe system including the same.

The present disclosure is to provide an optical probe capable of preventing signal distortion due to stress of an optical fiber and an optical probe system including the same.

An embodiment of the inventive concept provides an optical probe including: an optical input/output unit; a rotation part spaced apart from the optical input/output unit in a first direction and including a reflection surface; and a transparent electrode provided around the reflection surface.

In an embodiment, the reflection surface may have an acute angle or obtuse angle with the first direction.

In an embodiment, the optical input/output unit may include a lens and an optical fiber extending in the first direction.

In an embodiment, the optical probe may further include a housing surrounding the optical input/output unit, the rotation part, and the transparent electrode.

In an embodiment, the optical probe may further include: a first power path located in the housing and extending in the first direction along the optical input/output unit; and a second power path located in the housing and extending in the first direction along the rotation part.

In an embodiment, the transparent electrode may be electrically connected to the first power path and the second power path.

In an embodiment, the transparent electrode may further extend in the first direction along the optical input/output unit and the rotation part.

In an embodiment, the transparent electrode may include an anode transparent electrode and a cathode transparent electrode, wherein the anode transparent electrode and the cathode transparent electrode may be spaced apart from each other in a second direction intersecting the first direction.

In an embodiment, a length of the transparent electrode extending along the first direction may be shorter than the optical input/output unit and the rotation part extending along the first direction.

In an embodiment, the housing may include a transparent material.

In an embodiment, the optical probe may further include an optical fiber bundle surrounding the optical fiber and the lens.

In an embodiment of the inventive concept, an optical probe system includes: an optical probe; and a light source unit configured to supply light to the optical probe, wherein the optical probe includes: an optical input/output unit; a rotation part spaced apart from the optical input/output unit in a first direction and including a reflection surface; and a transparent electrode provided around the reflection surface.

In an embodiment, the optical probe system may further include a control unit for controlling the light source unit and the optical probe.

In an embodiment, the optical input/output unit may include a lens and an optical fiber extending in the first direction.

In an embodiment, the optical probe may further include a housing surrounding the optical input/output unit, the rotation part, and the transparent electrode.

In an embodiment, the optical probe may further include: a first power path located in the housing and extending in the first direction along the optical input/output unit; and a second power path located in the housing and extending in the first direction along the rotation part.

In an embodiment, the transparent electrode may be electrically connected to the first power path and the second power path.

BRIEF DESCRIPTION OF THE FIGURES

The accompanying drawings are included to provide a further understanding of the inventive concept, and are incorporated in and constitute a part of this specification. The drawings illustrate exemplary embodiments of the inventive concept and, together with the description, serve to explain principles of the inventive concept. In the drawings.

DETAILED DESCRIPTION

Figure 1:
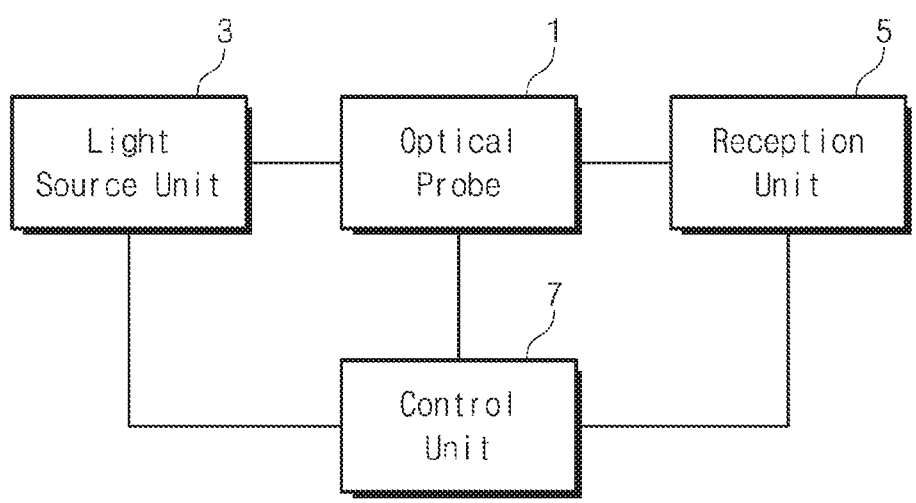
FIG. 1 is a conceptual diagram illustrating an optical probe and an optical probe system including the same according to exemplary embodiments of the inventive concept.

In order to fully understand the configuration and effects of the technical spirit of the inventive concept, preferred embodiments of the technical spirit of the inventive concept will be described with reference to the accompanying drawings. However, the technical spirit of the inventive concept is not limited to the embodiments set forth herein and may be implemented in various forms and various modifications may be applied thereto. Only, the technical spirit of the inventive concept is disclosed to the full through the description of the embodiments, and it is provided to those skilled in the art that the inventive concept belongs to inform the scope of the inventive concept completely.

Like reference numerals refer to like elements throughout the specification. Embodiments described herein will be described with reference to a perspective view, a front view, a sectional view, and/or a conceptual view, which are ideal examples of the technical idea of the inventive concept. In the drawings, the thicknesses of areas are exaggerated for effective description. Areas exemplified in the drawings have general properties, and are used to illustrate a specific shape of a semiconductor package region. Thus, this should not be construed as limited to the scope of the inventive concept. It will be understood that various terms are used herein to describe various components but these components should not be limited by these terms. These terms are just used to distinguish a component from another component. Embodiments described herein include complementary embodiments thereof.

The terms used in this specification are used only for explaining specific embodiments while not limiting the inventive concept. The terms of a singular form may include plural forms unless referred to the contrary. The meaning of "comprises," and/or "comprising" in this specification specifies the mentioned component but does not exclude at least one another component.

Hereinafter, preferred embodiments of the technical spirit of the inventive concept are described with reference to the accompanying drawings so that the inventive concept is described in more detail.

FIG. 1 is a conceptual diagram illustrating an optical probe and an optical probe system including the same according to exemplary embodiments of the inventive concept.

Referring to FIG. 1, an optical probe system may include an optical probe 1, a light source unit 3, a reception unit 5, and a control unit 7. The optical probe 1 may be inserted into a body to irradiate light, and may receive light reflected by an organ, a blood vessel, a living tissue, or the like. The light source unit 3 may supply light to the optical probe 1. In embodiments, the light source unit 3 may provide visible or near-infrared light. However, the inventive concept is not limited thereto, and electromagnetic waves having different wavelengths may be supplied. The reception unit 5 may receive light supplied from the light source unit 3 and reflected from the light source unit 3 after irradiated by the optical probe 1. The control unit 7 may control the optical probe 1, the light source unit 3, and the reception unit 5. That is, the light supplied from the light source unit 3 is irradiated to the object to be detected in the body from the optical probe 1, and the reflected light may be received by the reception unit 5 through the optical probe 1. The control unit 7 controls these processes and may interpret the light received by the reception unit 5 to implement a 3D model and the like. Hereinafter, the specific configuration of the optical probe 1 will be described in detail.

Figure 2:
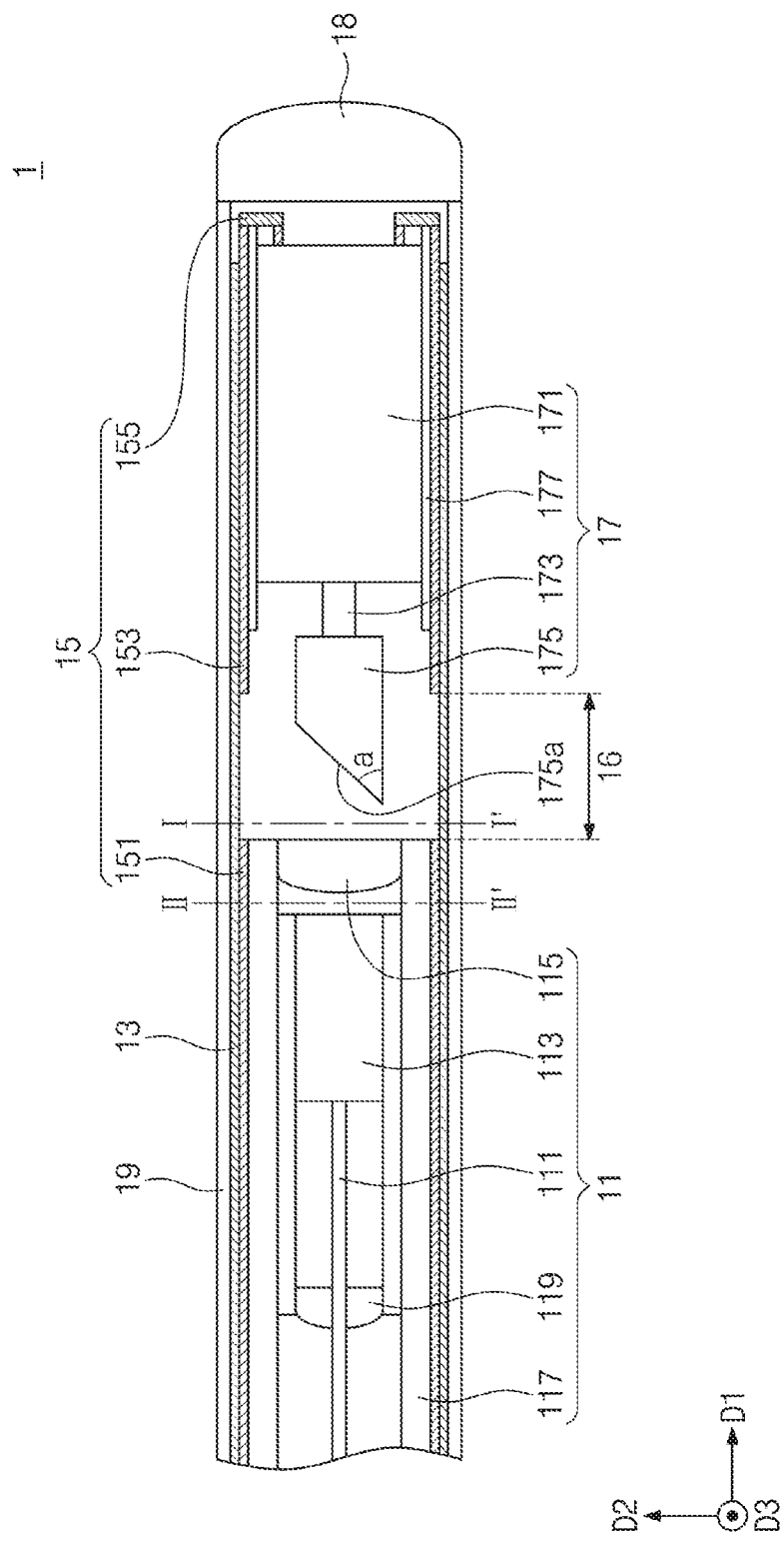
FIG. 2 is a cross-sectional view of an optical probe according to exemplary embodiments of the inventive concept.

FIG. 2 is a cross-sectional view of an optical probe according to exemplary embodiments of the inventive concept.

Hereinafter, the right side of FIG. 2 may be referred to as a first direction D1, the upper side may be referred to as a second direction D2, a direction that is orthogonal to the first direction D1 and the second direction D2 and faces the front may be referred to as a third direction D3. The first direction D1 may be referred to as the right side, the second direction D2 may be referred to as the upper side, and the third direction D3 may be referred to as the front side.

Referring to FIG. 2, the optical probe 1 includes a housing 19, an optical input/output unit 11, a rotation part 17, a transparent electrode 13, a power path 15, and a stopper 18.

The housing 19 may extend in the first direction D1. The housing 19 may have a hollow pillar shape. In embodiments, the cross-section of the housing 19 may be circular in shape. However, the inventive concept is not limited thereto. At least a portion of the housing 19 may be transparent. It is possible to detect the outside of the housing 19 inside the housing 19 through the transparent portion. In embodiments, the entire housing 19 may be transparent.

The optical input/output unit 11 may be located within the housing 19. The optical input/output unit 11 may extend along the first direction D1. The optical input/output unit 11 may irradiate light or receive reflected light after irradiation. The optical input/output unit 11 may irradiate the light in the first direction D1. The optical input/output unit 11 may include an optical fiber 111, lenses 113 and 115, an input/output housing 117, and a fixing means 119.

The optical fiber 111 may extend in the first direction D1. The light may move along the optical fiber 111. The light generated in the light source unit 3 may move along the optical fiber 111 in the first direction D1 and may be irradiated to a detection target. The light reflected by the detection target may move in the opposite direction of the first direction D1 along the optical fiber 111 and may be received by the reception unit 5 (see FIG. 1).

The lens may include a first lens 113 and a second lens 115. The first lens 113 may be disposed at one end of the optical fiber 111. The first lens 113 may prevent light emitted from the optical fiber 111 from diverging. In embodiments, the first lens 113 may include GRIN-Lens. The second lens 115 may be spaced from the first lens 113 in the first direction D1. The second lens 115 may refract light emitted through the first lens 113. The light emitted through the second lens 115 may be focused to one side. The focused light may be irradiated in the first direction D1 towards the rotation part 17.

The input/output housing 117 may extend in the first direction D1. The input/output housing 117 may include an insulating material. The input/output housing 117 may surround the optical fiber 111 and the lenses 113 and 115. The optical fiber 111 and the lenses 113 and 115 may be protected from external shock or the like by the input/output housing 117. The optical fiber 111 and the lenses 113 and 115 may be electrically isolated from the power path 15 by the input/output housing 117. The fixing means 119 may be located in the input/output housing 117. The fixing means 119 may fix the optical fiber 111 at a predetermined position.

The rotation part 17 may be located in the housing 19. The rotation part 17 may be spaced from the input/output housing 117 in the first direction D1. The rotation part 17 may be rotated using the first direction D1 as an axis. The rotation part 17 may include a rotation means 171, a rotation axis 173, a rotation mirror 175 and an insulating layer 177.

The rotation means 171 may rotate the rotation mirror 175 by receiving power from the power path 15 or the like. In embodiments, the rotation means 171 may include a micro-motor.

The rotation axis 173 may extend from the rotation means 171 in a direction opposite to the first direction D1. The rotation axis 173 may connect the rotation means 171 and the rotation mirror 175. The rotation axis 173 may be rotated by the rotation means 171.

The rotation axis 173 may extend from the rotation means 171 in a direction opposite to the first direction D1. The rotation mirror 175 may reflect the light irradiated by the optical input/output unit 11. The rotation mirror 175 may reflect the reflected light from the detection target T (see FIG. 5) and irradiate it to the optical input/output unit 11. The rotation mirror 175 may be rotated by the rotation axis 173. The rotation mirror 175 may include a reflection surface 175a. The reflection surface 175a may have a constant angle a with respect to the first direction D1. a may not be 90 degrees. a may be acute or obtuse. Preferably, a may be 45 degrees. When a is 45 degrees, the light irradiated from the optical input/output unit 11 may be reflected in a direction perpendicular to the first direction D1. However, the inventive concept is not limited thereto.

The insulating layer 177 may surround the rotation means 171. The insulating layer 177 may include an insulating material. The insulating layer 177 may protect the rotation means 171 from external shocks and the like. The insulating layer 177 may electrically insulate the rotation means 171 from the power path 15.

The transparent electrode 13 may be located in the housing 19. The transparent electrode 13 may include a conductive material. The transparent electrode 13 may be provided around the reflection surface 175a. More specifically, the transparent electrode 13 may be positioned in a direction perpendicular to the first direction D1 from the portion where the reflection surface 175a is located. Thus, the transparent electrode 13 may surround the reflection surface 175a. The transparent electrode 13 may extend in the first direction D1 from the side of the optical input/output unit 11 toward the side of the rotation part 17.

The peripheral area of the reflection surface 175a surrounded by the transparent electrode 13 may be referred to as an optical window part 16. The optical window part 16 may be located between the optical input/output unit 11 and the rotation part 17. Light reflected at the reflection surface 175a may be irradiated outside the optical probe 1 through the transparent electrode 13. That is, the light may be introduced through the optical window part 16. In embodiments, the transparent electrode 13 may extend further along the optical input/output unit 11 and/or the rotation part 17 in the first direction D1. Details of the transparent electrode 13 will be described later with reference to FIGS. 3 to 6.

The power path 15 may be located in the housing 19. The power path 15 may include a conductive material. The power path 15 may have a very low electrical resistance. The electrical resistance of the power path 15 may be lower than the electrical resistance of the transparent electrode 13. In embodiments, the power path 15 may include an opaque material. The power path 15 may include a first power path 151, a second power path 153, and a connection power path 155. The first power path 151 may extend along the optical input/output unit 11 in a first direction D1. The first power path 151 may transmit power in the first direction D1. The second power path 153 may extend along the rotation part 17 in the first direction D1. The connection power path 155 may connect the second power path 153 and the rotation means 171. The connection power path 155 may receive power from the first power path 153 and supply the power to the rotation means 171. Details of the power path 15 will be described later with reference to FIGS. 3 to 6.

The stopper 18 may be spaced from the rotation part 17 in the first direction D1. The stopper 18 may be coupled to one side of the housing 19. The stopper 18 may seal the inside of the housing 19.

Figure 3:
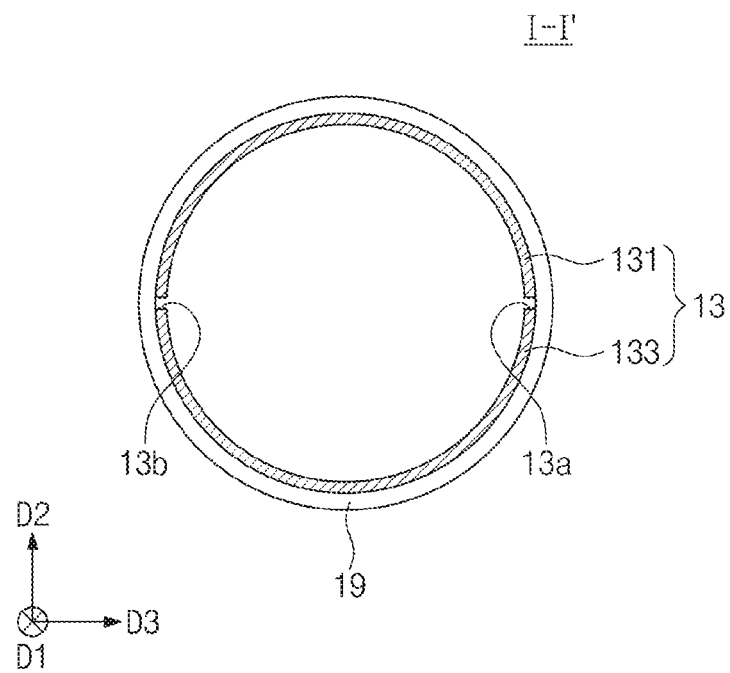
FIG. 3 is a cross-sectional view of an optical probe taken along a line I-I' of FIG. 2 according to exemplary embodiments of the inventive concept.

FIG. 3 is a cross-sectional view of an optical probe taken along a line I-I' of FIG. 2 according to exemplary embodiments of the inventive concept.

Referring to FIG. 3, the transparent electrode 13 may be coupled to the housing 19. The transparent electrode 13 may be deposited or bonded to the inner surface of the housing 19 in the form of a thin film. The transparent electrode 13 may include an anode transparent electrode 131 and a cathode transparent electrode 133. The anode transparent electrode 131 and the cathode transparent electrode 133 may be approximately semicircular in shape. The anode transparent electrode 131 and the cathode transparent electrode 133 may be spaced apart in the second direction D2. The anode transparent electrode 131 and the cathode transparent electrode 133 may be separated by the first separation part 13a and the second separation part 13b. The anode transparent electrode 131 and the cathode transparent electrode 133 may be electrically separated by the first separation part 13a and the second separation part 13b. In embodiments, the first separation part 13a and the second separation part 13b may include an insulator. In embodiments, the first separation part 13a and the second separation part 13b may include an insulator.

Figure 4:
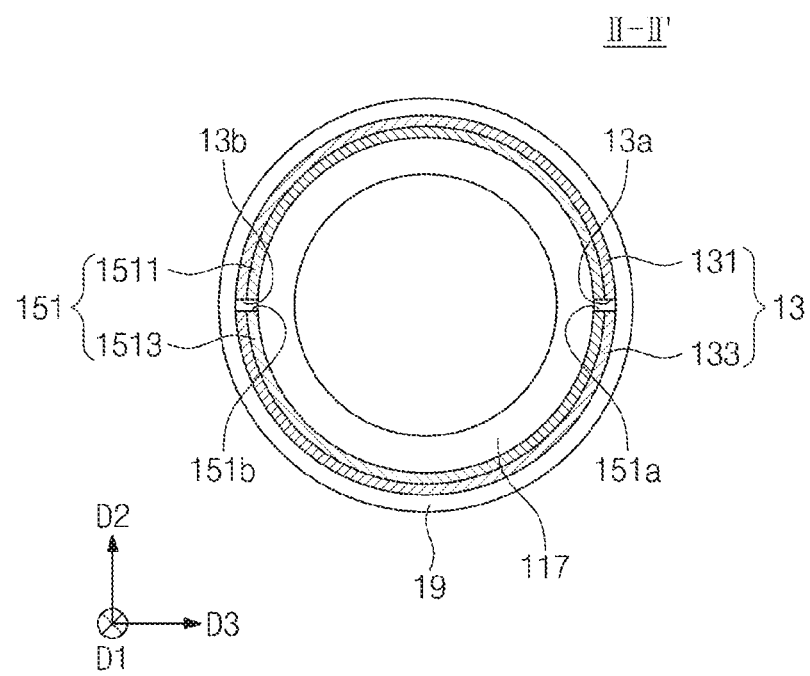
FIG. 4 is a cross-sectional view of an optical probe taken along a line II-II' of FIG. 2 according to exemplary embodiments of the inventive concept.

FIG. 4 is a cross-sectional view of an optical probe taken along a line II-II' of FIG. 2 according to exemplary embodiments of the inventive concept.

Referring to FIG. 4, the first power path 151 may be coupled to the transparent electrode 13. The first power path 151 may be press-bonded or epoxy-bonded to the inner surface of the transparent electrode 13. The first power path 151 may include an anode first power path 1511 and a cathode first power path 1513. The anode first power path 1511 and the cathode first power path 1513 may be approximately semicircular in shape. The anode first power path 1511 and the cathode first power path 1513 may be spaced apart in the second direction D2. The anode first power path 1511 and the cathode first power path 1513 may be separated by the third separation part 151a and the fourth separation part 151b. The anode first power path 1511 and the cathode first power path 1513 may be electrically separated by the third separation part 151a and the fourth separation part 151b. The third separation part 151a and the fourth separation part 151b may include an insulator. In embodiments, the third separation part 151a and the fourth separation part 151b may include epoxy or air. The third separation part 151a and the fourth separation part 151b may be connected to the first separation part 13a and the second separation part 13b, respectively.

Figure 5:
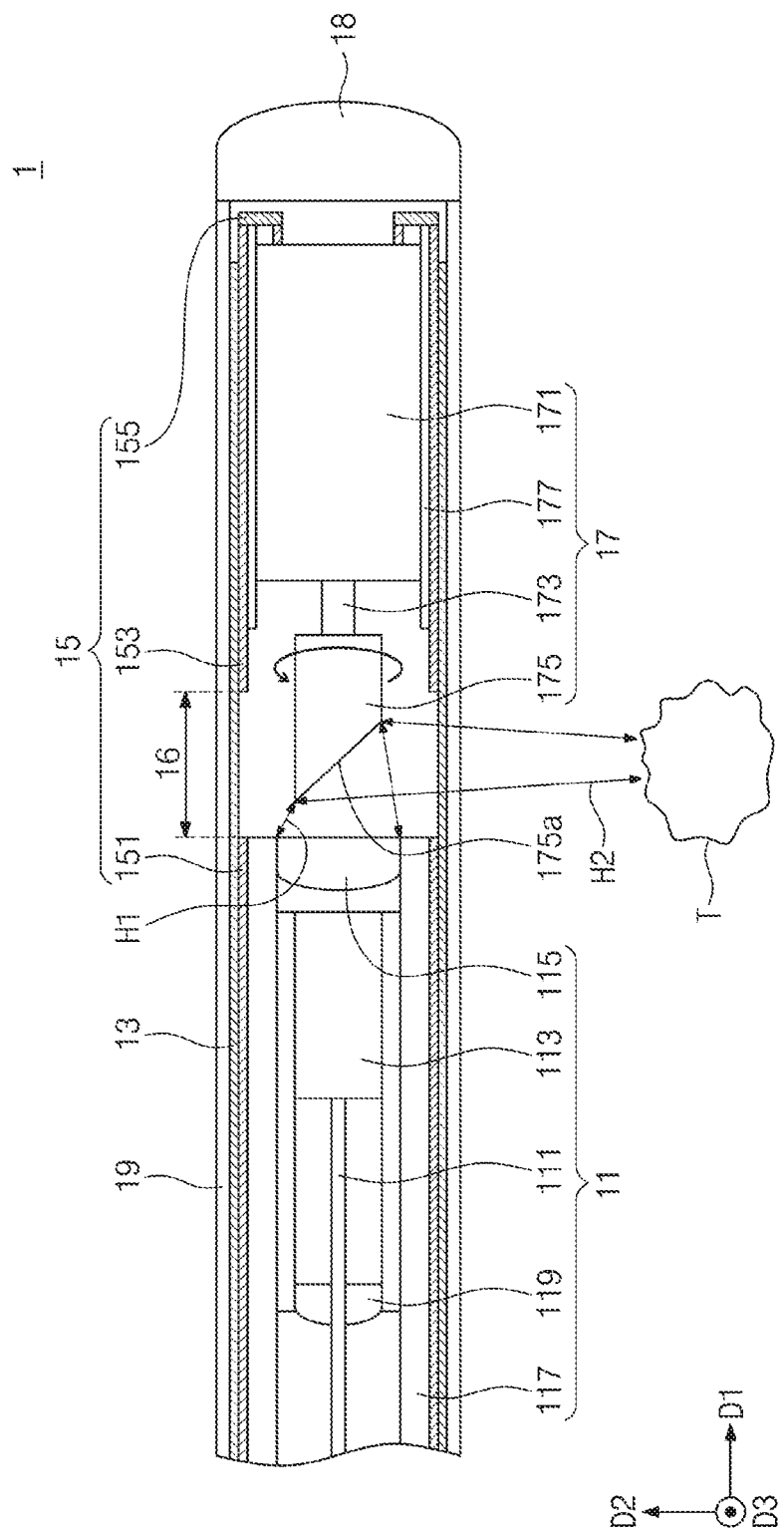
FIG. 5 is a cross-sectional view illustrating the operation principle of an optical probe according to exemplary embodiments of the inventive concept.

FIG. 5 is a cross-sectional view illustrating the operation principle of an optical probe according to exemplary embodiments of the inventive concept.

Referring to FIG. 5, the light emitted from the light source unit 3 (see FIG. 1) may move along the optical fiber 111. The light H1 emitted through the lenses 113 and 115 may be irradiated in the direction of the rotation mirror 175. The light H2 reflected from the reflection surface 175a is emitted through the transparent electrode 13 and reaches the detection target T. That is, the light H2 may exit to the outside of the optical probe 1 in the optical window part 16. The light H2 may be reflected by the detection target T and back to the reflection surface 175a. That is, the light H2 may enter the optical probe 1 again in the optical window part 16. The light H1 reflected back to the reflection surface 175a is moved to the reception unit 5 (see FIG. 1) through the optical fiber 111. At this time, power is supplied to the rotation means 171 through the first power path 151, the transparent electrode 13, the second power path 153, and the connection power path 155, and the rotation means 171 rotates the rotation mirror 175. Accordingly, the light may be irradiated in all directions perpendicular to the first direction D1 according to the rotation of the reflection surface 175a.

According to the optical probe according to the exemplary embodiments of the inventive concept, since the light reflected by the reflection surface 175a uses a transparent electrode 13 at the exit of the housing 19, it may be prevented that the light irradiation is obstructed by the opaque power path 15 to generate the shadow. The reflection surface 175a rotates 360 degrees to uniformly irradiate light to the entire area. Detection by the optical probe 1 may be more accurate.

Depending on the optical probe according to the exemplary embodiments of the inventive concept, since the rotation means 171 rotates only the rotation mirror 175, occurrence of signal distortion due to stress according to rotation of the optical fiber 111 may be prevented. Since only the rotation part 17 rotates, faster rotation may be possible. The data obtained by the detection of the optical probe 1 may be more accurate.

Depending on the optical probe according to the exemplary embodiments of the inventive concept, since the power path 15 with lower electrical resistance than the transparent electrode 13 is used together while the transparent electrode 13 is used, the overall electrical resistance may be lowered. The length of the portion where only the transparent electrode 13 is used may be minimized, such that the rise of electrical resistance may be suppressed.

Figure 6:
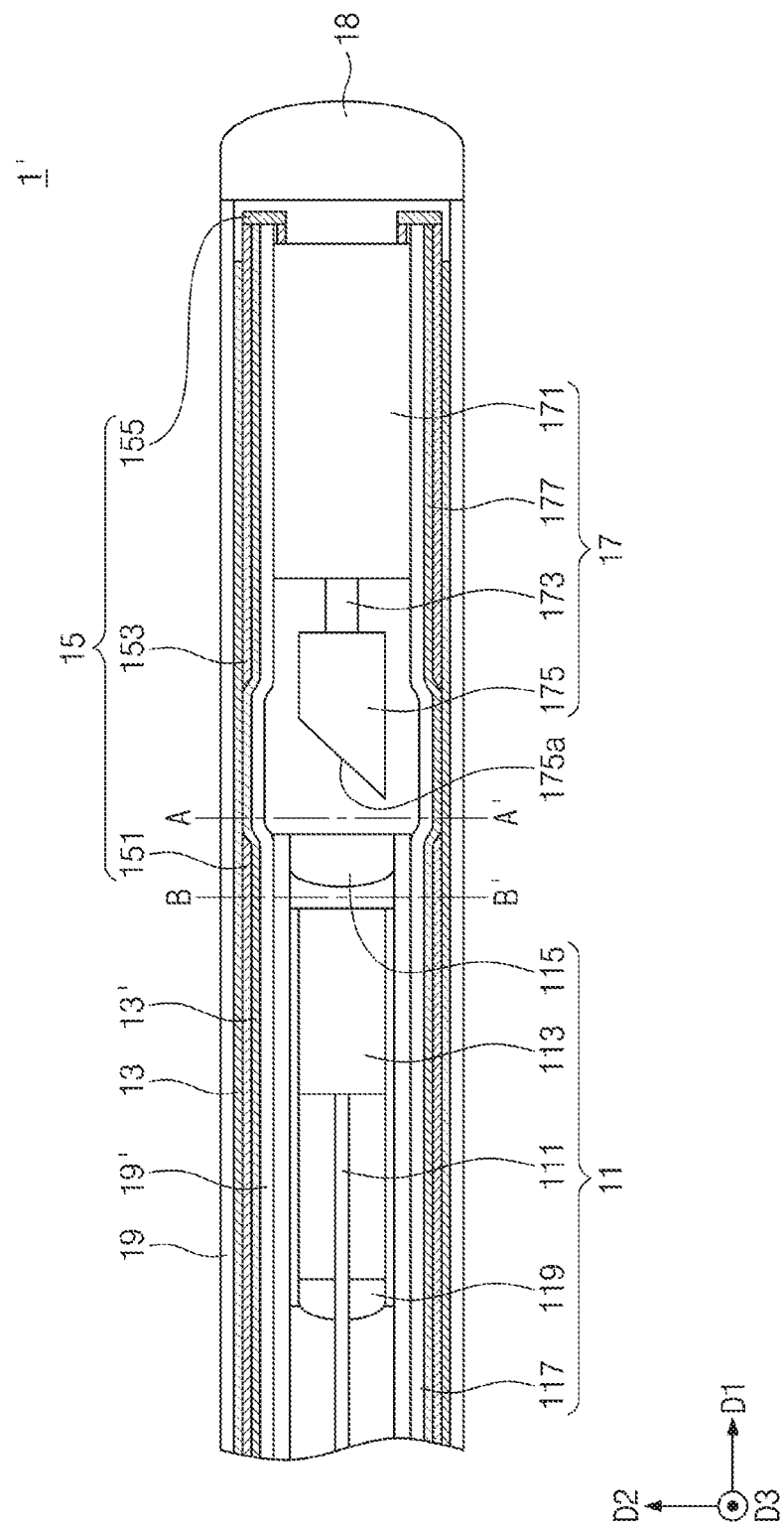
FIG. 6 is a cross-sectional view of an optical probe according to exemplary embodiments of the inventive concept.

FIG. 6 is a cross-sectional view of an optical probe according to exemplary embodiments of the inventive concept.

Hereinafter, substantially the same or similar contents as those described with reference to FIGS. 1 to 5 may be omitted for convenience of explanation.

Referring to FIG. 6, the optical probe 1' may further include an inner transparent electrode 13'. The inner transparent electrode 13' may be coupled to the inner surfaces of the first power path 151 and the second power path 153. In the A-A' region, the transparent electrode 13 and the inner transparent electrode 13' may be combined. Details will be described later with reference to FIGS. 7 and 8.

Figure 7:
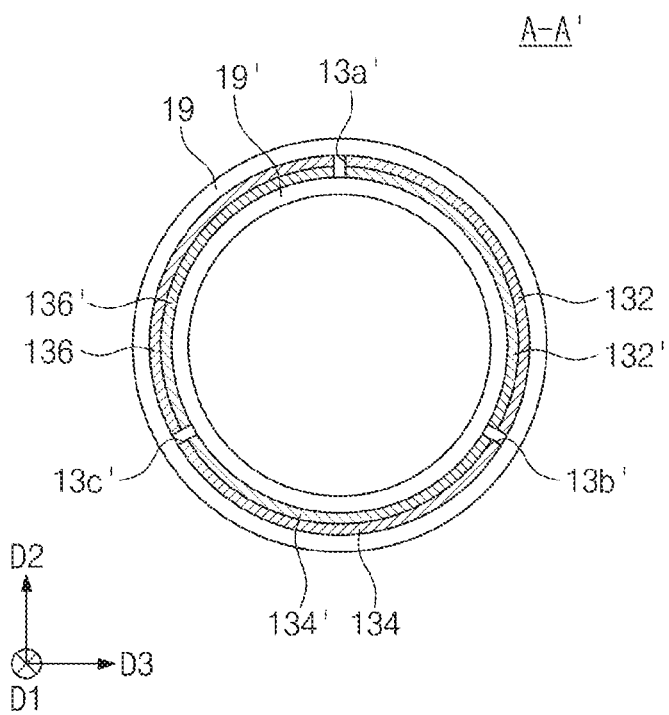
FIG. 7 is a cross-sectional view of an optical probe taken along a line A-A' of FIG. 6 according to exemplary embodiments of the inventive concept.

FIG. 7 is a cross-sectional view of an optical probe taken along a line A-A' of FIG. 6 according to exemplary embodiments of the inventive concept.

Referring to FIG. 7, the transparent electrode 13 (see FIG. 6) may include a first transparent electrode 132, a second transparent electrode 134, and a third transparent electrode 136. The first transparent electrode 132 and the second transparent electrode 134 may be separated by a second separation part 13b'. The second transparent electrode 134 and the third transparent electrode 136 may be separated by a third separation part 13c'. The third transparent electrode 136 and the first transparent electrode 132 may be separated by a first separation part 13a'. In embodiments, each of the first to third transparent electrodes 132, 134, 136 may be in the form of a one-third circle. Each of the first to third separation parts 13a', 13b', 13c' may include an insulator. In embodiments, each of the first to third separation parts 13a', 13b', and 13c' may include epoxy or air or the like. Each of the first to third transparent electrodes 132, 134, and 136 may provide a three-phase power path.

The inner transparent electrode 13' (see FIG. 6) may include a first inner transparent electrode 132', a second inner transparent electrode 134', and a third inner transparent electrode 136'. Each of the first to third inner transparent electrodes 132 ', 134', and 136' may be coupled to the inner surface of each of the first to third transparent electrodes 132, 134, and 136. Each of the first to third inner transparent electrodes 132', 134', and 136' may be spaced apart from each other by each of the first to third separation parts 13a', 13b', and 13c'. Since the transparent electrode 13 and the inner transparent electrode 13' are used, the total thickness of the transparent electrode may be increased. The electrical resistance of the transparent electrode may be reduced. Electrical losses due to the resistance of the transparent electrode may be reduced.

Figure 8:
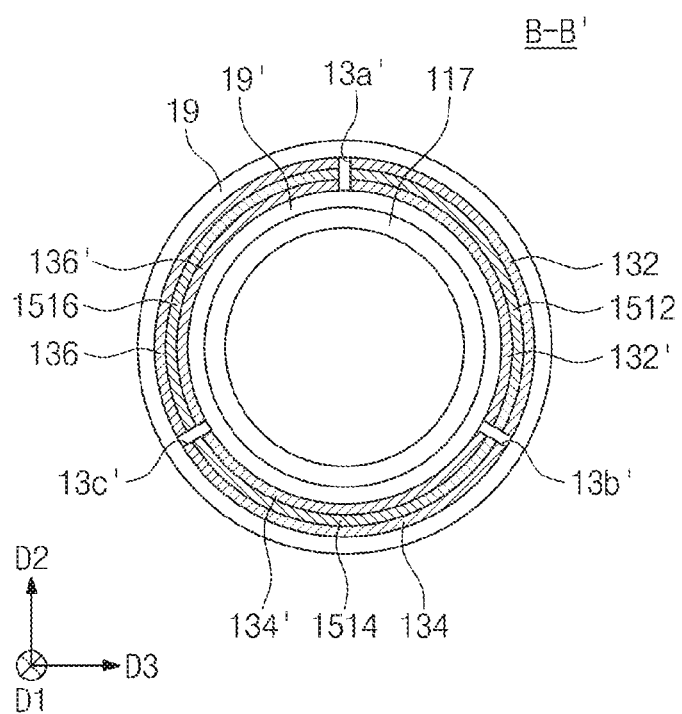
FIG. 8 is a cross-sectional view of an optical probe taken along a line B-B' of FIG. 6 according to exemplary embodiments of the inventive concept.

FIG. 8 is a cross-sectional view of an optical probe taken along a line B-B' of FIG. 6 according to exemplary embodiments of the inventive concept.

Referring to FIG. 8, a first power path 151 may be located between the transparent electrode 13 and the inner transparent electrode 13'. The first power path 151 may include a 1-1 power path 1512, a 1-2 power path 1514, and a 1-3 power path 1516. Each of the 1-1 to 1-3 power paths 1512, 1514, and 1516 may be bonded to the inner surfaces of the first to third transparent electrodes 132, 134, and 136 by press bonding or epoxy bonding. Each of the 1-1 to 1-3 power paths 1512, 1514, and 1516 may be spaced apart from each other by each of the first to third separation parts 13a', 13b', and 13c'. Each of the 1-1 to 1-3 power paths 1512, 1514, and 1516 may provide a three-phase power path.

Figure 9:
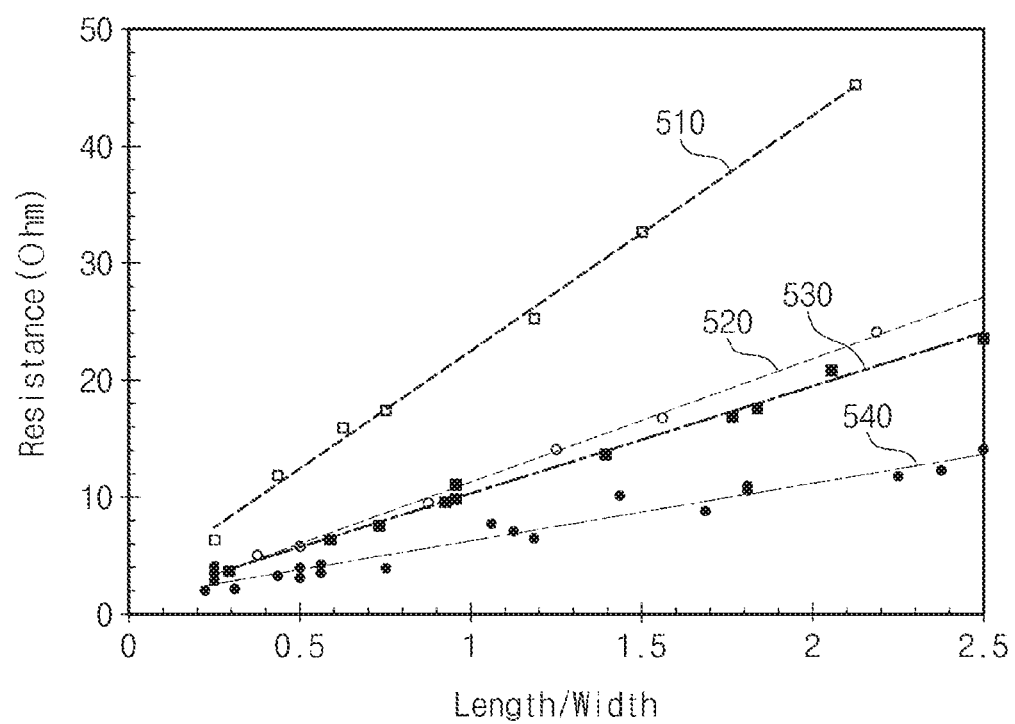
FIG. 9 is a graph showing experimental results of electrical resistance for an optical probe according to exemplary embodiments of the inventive concept.

FIG. 9 is a graph showing experimental results of electrical resistance for an optical probe according to exemplary embodiments of the inventive concept.

The horizontal axis of the graph of FIG. 9 may mean the ratio of the length of the transparent electrode 13 (see FIGS. 2 to 5) in the first direction D1 to the width perpendicular to the first direction D1. The vertical axis may refer to the overall electrical resistance (Ohm) when the power electrode 15 (see FIGS. 2 to 5) is coupled to the transparent electrode 13. The optical transmittance of the transparent electrode 13 used in this experiment may be approximately 80% or more in the visible and near infrared regions. The electrical resistance of the transparent electrode 13 may be approximately 10 Ohm/sq. The electrical resistance of the power path 15 may be very low. The power path 15 may be substantially a non-resistive conductor.

The first trend line 510 of FIG. 9 may refer to the length/width ratio and the resistance according thereto when the power path 15 is bonded to the transparent electrode through compression bonding. The second trend line 520 may refer to the length/width ratio and the resistance according thereto when the power path 15 is bonded to the transparent electrode through conductive epoxy. The first trend line 510 and the second trend line 520 may correspond to the embodiment of the one-layer transparent electrode described with reference to FIGS. 2 to 5.

The first trend line 510 of FIG. 9 may refer to the length/width ratio and the resistance according thereto when the power path 15 is bonded between two-layer transparent electrodes through compression bonding. The fourth trend line 540 may refer to the length/width ratio and the resistance according thereto when the power path 15 is bonded between two-layer transparent electrodes through conductive epoxy. The third trend line 530 and the fourth trend line 540 may correspond to the embodiment of the two-layer transparent electrode described with reference to FIGS. 6 to 8.

In the first to fourth trend lines 510, 520, 530, and 540, as the length/width ratio of the transparent electrode becomes larger, the electrical resistance may increase. That is, as the length of the transparent electrode is shorter and the width is larger, the electrical resistance may decrease.

When comparing the first trend line 510 and the second trend line 520, as compared to using compression bonding, when using conductive epoxy, the electrical resistance may be lower at the same length/width. This may be the same case when the third trend line 530 and the fourth trend line 540 are compared.

When comparing the first trend line 510 and the third trend line 530, as compared to using a one-layer transparent electrode, when using a two-layer transparent electrode, the electrical resistance may be lower at the same length/width. This may be the same case when the second trend line 520 and the fourth trend line 540 are compared.

Figure 10:
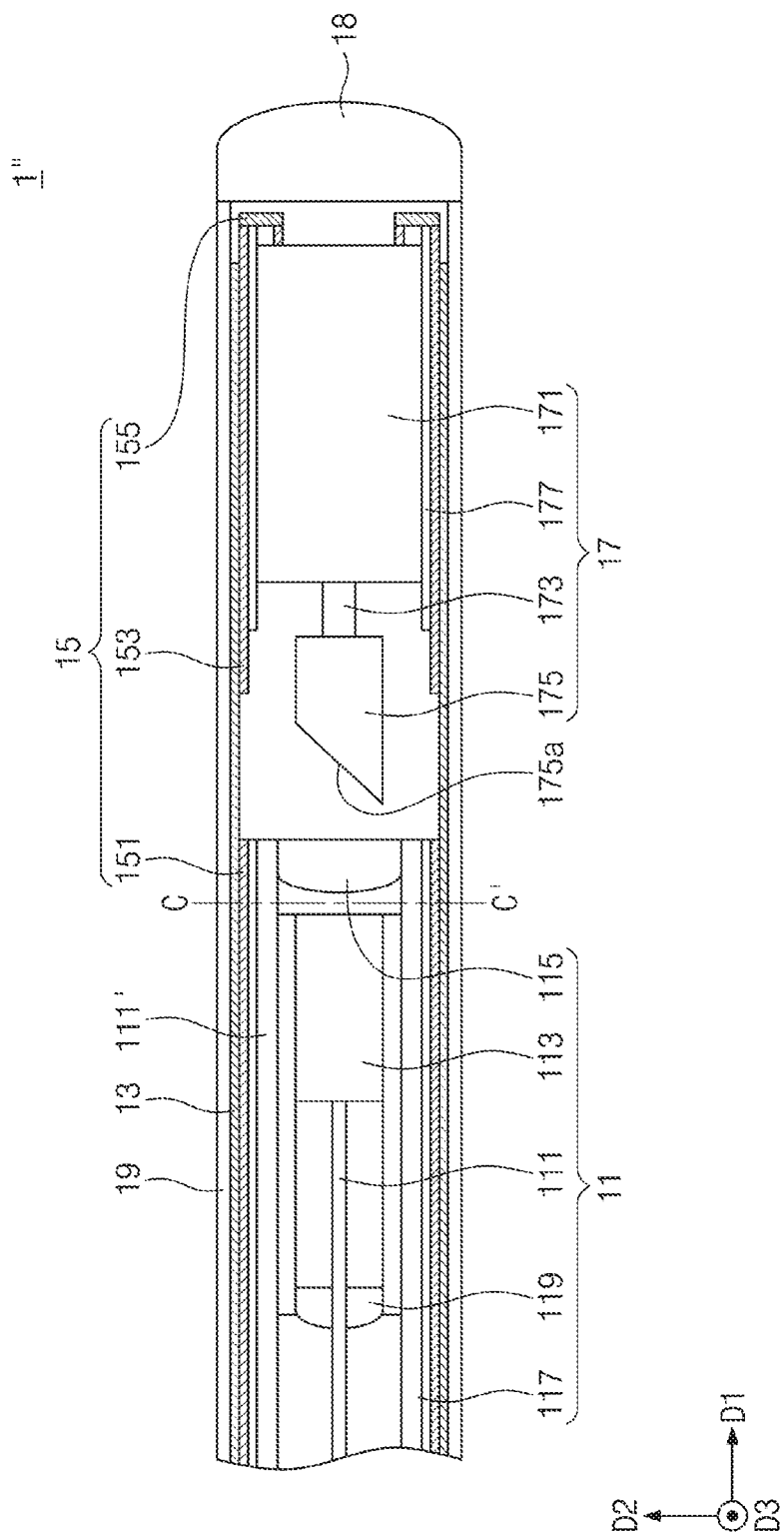
FIG. 10 is a cross-sectional view of an optical probe according to exemplary embodiments of the inventive concept.

FIG. 10 is a cross-sectional view of an optical probe according to exemplary embodiments of the inventive concept.

Hereinafter, substantially the same or similar contents as those described with reference to FIGS. 1 to 5 may be omitted for convenience of explanation.

Referring to FIG. 10, an optical probe 1" may further include an optical fiber bundle 111'. The optical fiber bundle 111' may be located outside the optical input/output unit 11. The optical fiber bundle 111' may extend in the first direction D1. The optical fiber bundle 111' may include a plurality of optical fibers. Details of the optical fiber bundle 111' will be described later with reference to FIG. 11.

Figure 11:
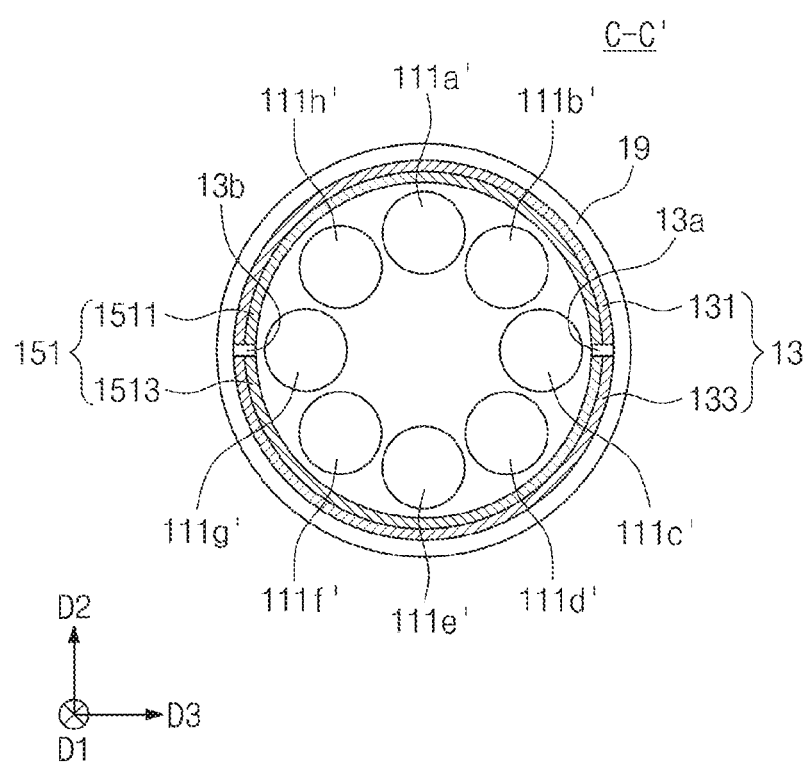
FIG. 11 is a cross-sectional view of an optical probe taken along a line C-C' of FIG. 10 according to exemplary embodiments of the inventive concept.

FIG. 11 is a cross-sectional view of an optical probe taken along a line C-C' of FIG. 10 according to exemplary embodiments of the inventive concept.

Referring to FIG. 11, the optical fiber bundle 111' (see FIG. 10) includes a first optical fiber 111a', a second optical fiber 111b', a third optical fiber 111c', a fourth optical fiber 111d', a fifth optical fiber 111e', a sixth optical fiber 111f, a seventh optical fiber 111g', and an eighth optical fiber 111h'. Although it is shown in FIG. 11 that the optical fiber bundle includes eight optical fibers, it is not limited thereto. That is, the optical fiber bundle may include a varying number of optical fibers.

The first optical fiber 111a' to the eighth optical fiber 111h' may be spaced apart from the optical input/output unit 11 by a predetermined distance. The first optical fiber 111a' to the eighth optical fiber 111h' may receive light that is reflected by the detection target and introduced through the reflection surface 175a. The amount of light received by the first optical fiber 111a' to the eighth optical fiber 111h' may increase. The accuracy of detection may be improved.

According to the optical probe of the inventive concept and the optical probe system including the same, a shadow may be eliminated from the light irradiation section.

According to the optical probe of the inventive concept and the optical probe system including the same, there is no shading section, so that all sections may be detected accurately.

According to the optical probe of the inventive concept and the optical probe system including the same, electrical characteristics such as resistance may be improved while using a transparent electrode.

According to the optical probe of the inventive concept and the optical probe system including the same, high-speed rotation is possible so that accurate images may be obtained.

According to the optical probe of the inventive concept and the optical probe system including the same, the signal distortion due to the stress of the optical fiber may be prevented.

The effects of the inventive concept are not limited to the effects mentioned above, and other effects not mentioned may be clearly understood by those skilled in the art from the following description.

Although the exemplary embodiments of the inventive concept have been described, it is understood that the inventive concept should not be limited to these exemplary embodiments but various changes and modifications may be made by one ordinary skilled in the art within the spirit and scope of the inventive concept as hereinafter claimed.

What is claimed is:

1. An optical probe comprising:
 an optical input/output unit;
 a rotation part spaced apart from the optical input/output unit in a first direction and including a reflection surface; and
 a transparent electrode surrounding the reflection surface.

2. The optical probe of claim 1, wherein the reflection surface has an acute angle or obtuse angle with the first direction.

3. The optical probe of claim 1, wherein the optical input/output unit comprises a lens and an optical fiber extending in the first direction.

4. The optical probe of claim 3, further comprising an optical fiber bundle surrounding the optical fiber and the lens.

5. The optical probe of claim 1, further comprising a housing surrounding the optical input/output unit, the rotation part, and the transparent electrode.

6. The optical probe of claim 5, further comprising:
 a first power path located in the housing and extending in the first direction along the optical input/output unit; and
 a second power path located in the housing and extending in the first direction along the rotation part.

7. The optical probe of claim 6, wherein the transparent electrode is electrically connected to the first power path and the second power path.

8. The optical probe of claim 7, wherein the transparent electrode further extends in the first direction along the optical input/output unit and the rotation part.

9. The optical probe of claim 5, wherein the housing comprises a transparent material.

10. The optical probe of claim 1, wherein the transparent electrode comprises an anode transparent electrode and a cathode transparent electrode,
wherein the anode transparent electrode and the cathode transparent electrode are spaced apart from each other in a second direction intersecting the first direction.

11. The optical probe of claim 1, wherein a length of the transparent electrode extending along the first direction is shorter than the optical input/output unit and the rotation part extending along the first direction.

12. The optical probe of claim 1, further comprising:
an optical window part located in the first direction relative to the optical input/output unit;
wherein the reflection surface is configured to reflect light transmitted from the optical input/output unit through the optical window part onto a detection target.

13. The optical probe of claim 1, wherein the rotation part is rotated using the first direction as an axis.

14. An optical probe system comprising:
an optical probe; and
a light source unit configured to supply light to the optical probe,
wherein the optical probe comprises:
an optical input/output unit;
a rotation part spaced apart from the optical input/output unit in a first direction and including a reflection surface; and
a transparent electrode surrounding the reflection surface.

15. The optical probe system of claim 14, further comprising a control unit for controlling the light source unit and the optical probe.

16. The optical probe system of claim 14, wherein the optical input/output unit comprises a lens and an optical fiber extending in the first direction.

17. The optical probe system of claim 14, wherein the optical probe further comprises a housing surrounding the optical input/output unit, the rotation part, and the transparent electrode.

18. The optical probe system of claim 17, wherein the optical probe further comprises:
a first power path located in the housing and extending in the first direction along the optical input/output unit; and
a second power path located in the housing and extending in the first direction along the rotation part.

19. The optical probe system of claim 18, wherein the transparent electrode is electrically connected to the first power path and the second power path.

* * * * *